(12) United States Patent
Brunker et al.

(10) Patent No.: US 9,061,141 B2
(45) Date of Patent: Jun. 23, 2015

(54) PATIENT SUPPORT DEVICE WITH LOW ATTENUATION PROPERTIES

(75) Inventors: Bradley J. Brunker, Madison, WI (US); Douglas James Henderson, Middleton, WI (US); Scott Peter Adler, Madison, WI (US)

(73) Assignee: TOMOTHERAPY INCORPORATED, Madison, WI (US)

( * ) Notice: Subject to any disclaimer, the term of this patent is extended or adjusted under 35 U.S.C. 154(b) by 404 days.

(21) Appl. No.: 12/893,658

(22) Filed: Sep. 29, 2010

(65) Prior Publication Data

US 2011/0107515 A1 May 12, 2011

Related U.S. Application Data

(60) Provisional application No. 61/246,927, filed on Sep. 29, 2009.

(51) Int. Cl.
*A61N 5/10* (2006.01)
*A61B 6/04* (2006.01)

(52) U.S. Cl.
CPC .............. *A61N 5/10* (2013.01); *Y10T 29/49826* (2015.01); *A61B 6/0407* (2013.01); *A61B 6/0457* (2013.01); *A61B 6/04* (2013.01); *A61B 6/0442* (2013.01)

(58) Field of Classification Search
CPC ..................... A61B 6/00–6/0492; A61N 5/10; Y10T 29/49826
USPC ........................ 5/601, 600; 378/204, 208–209
See application file for complete search history.

(56) References Cited

U.S. PATENT DOCUMENTS

| | | | |
|---|---|---|---|
| 4,149,081 | A | 4/1979 | Seppi |
| 4,998,268 | A | 3/1991 | Winter |
| 5,008,907 | A | 4/1991 | Norman et al. |
| 5,044,354 | A | 9/1991 | Goldhorn et al. |
| 5,065,315 | A | 11/1991 | Garcia |
| 5,117,829 | A | 6/1992 | Miller et al. |
| 5,317,616 | A | 5/1994 | Swerdloff et al. |

(Continued)

FOREIGN PATENT DOCUMENTS

| | | |
|---|---|---|
| DE | 19808042 A1 * | 9/1999 |
| JP | 2002210029 | 7/2002 |

(Continued)

OTHER PUBLICATIONS

Purdy, James, "3D Treatment Planning and Intensity-Modulated Radiation Therapy," Oncology, vol. 13, No. 10, suppl. 5 (Oct. 1999).

(Continued)

*Primary Examiner* — Peter M Cuomo
*Assistant Examiner* — Brittany Wilson
(74) *Attorney, Agent, or Firm* — Michael Best & Friedrich LLP

(57) ABSTRACT

A patient support device for a radiation therapy treatment system and a method of manufacturing the same. The device includes a support having an upper surface and a lower surface and a fixture hole configuration that receives a patient fixation device. The fixture hole configuration includes at least one recess and reinforcing material positioned inside at least a portion of the at least one recess. The device may also include a lower support having an upper surface that includes at least one channel. Flat flex cable used to operate the patient support device is positioned within the at least one channel.

19 Claims, 14 Drawing Sheets

(56) References Cited

U.S. PATENT DOCUMENTS

| | | |
|---|---|---|
| 5,332,908 A | 7/1994 | Weidlich |
| 5,335,255 A | 8/1994 | Seppi et al. |
| 5,351,280 A | 9/1994 | Swerdloff et al. |
| 5,391,139 A | 2/1995 | Edmundson |
| 5,394,452 A | 2/1995 | Swerdloff et al. |
| 5,405,309 A | 4/1995 | Carden, Jr. |
| 5,442,675 A | 8/1995 | Swerdloff et al. |
| 5,446,548 A | 8/1995 | Gerig et al. |
| 5,471,516 A | 11/1995 | Nunan |
| 5,511,549 A | 4/1996 | Legg et al. |
| 5,528,650 A | 6/1996 | Swerdloff et al. |
| 5,548,627 A | 8/1996 | Swerdloff et al. |
| 5,552,605 A | 9/1996 | Arata |
| 5,579,358 A | 11/1996 | Lin |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,647,663 A | 7/1997 | Holmes |
| 5,651,043 A | 7/1997 | Tsuyuki et al. |
| 5,661,773 A | 8/1997 | Swerdloff et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,712,482 A | 1/1998 | Gaiser et al. |
| 5,724,400 A | 3/1998 | Swerdloff et al. |
| 5,751,781 A | 5/1998 | Brown et al. |
| 5,754,623 A | 5/1998 | Seki |
| 5,760,395 A | 6/1998 | Johnstone |
| 5,823,192 A | 10/1998 | Kalend et al. |
| 5,835,562 A | 11/1998 | Ramsdell et al. |
| 5,983,424 A | 11/1999 | Naslund |
| 6,045,262 A | 4/2000 | Iget et al. |
| 6,152,599 A | 11/2000 | Salter, Jr. |
| 6,155,976 A | 12/2000 | Sackner et al. |
| 6,385,288 B1 | 5/2002 | Kanematsu |
| 6,405,072 B1 | 6/2002 | Cosman |
| 6,615,428 B1 | 9/2003 | Pattee |
| 6,634,790 B1 | 10/2003 | Salter, Jr. |
| 6,637,056 B1 | 10/2003 | Tybinkowski et al. |
| 6,769,145 B1 | 8/2004 | Pfeuffer et al. |
| 6,895,617 B2 | 5/2005 | Zacharopoulos et al. |
| 6,955,464 B1 | 10/2005 | Tybinkowski et al. |
| 7,367,955 B2 | 5/2008 | Zhang et al. |
| 7,437,785 B2 | 10/2008 | Farooqui |
| 7,492,858 B2 | 2/2009 | Partain et al. |
| 7,519,150 B2 | 4/2009 | Romesberg et al. |
| 7,640,607 B2 | 1/2010 | Guertin et al. |
| 7,784,127 B2 | 8/2010 | Kuro et al. |
| 7,792,239 B2 * | 9/2010 | Nambu et al. ............... 378/4 |
| 8,122,542 B2 | 2/2012 | Reitz et al. |
| 2004/0057557 A1 | 3/2004 | Nafstadius |
| 2007/0041496 A1 | 2/2007 | Olivera et al. |
| 2007/0127790 A1 | 6/2007 | Lu et al. |
| 2008/0279328 A1 | 11/2008 | Zeitler et al. |
| 2010/0053208 A1 | 3/2010 | Menningen et al. |
| 2010/0054413 A1 | 3/2010 | Sobering et al. |
| 2010/0319128 A1 | 12/2010 | Kuro et al. |
| 2011/0019889 A1 | 1/2011 | Gering et al. |

FOREIGN PATENT DOCUMENTS

| | | |
|---|---|---|
| JP | 2004166975 | 6/2004 |
| TW | 300853 | 3/1997 |
| WO | 03032838 | 4/2003 |

OTHER PUBLICATIONS

Lee, Jason et al., "Intensity Modulated Radiation Therapy; An Introduction for Patients and Clinicians," www.oncolink.com/templates/treatment/article.cfm?c=45&s=33&id=182; Jun. 16, 2001.

Keall, Paul, "4-Dimensional Computed Tomography Imaging and Treatment Planning," Seminars in Radiation Oncology, vol. 14, No. 1, Jan. 2004; pp. 81-90.

Mackie, T. Rockwell et al., "Tomotherapy: Rethinking the Processes of Radiotherapy," XIIth ICCR, May 27-30, 1997.

Fang, Guang Y. et al., "Software system for the UW/GE tomotherapy prototype," XIith ICCR, May 27-30, 1997.

PCT/US2010/050721 International Search Report and Written Opinion dated May 20, 2011.

* cited by examiner

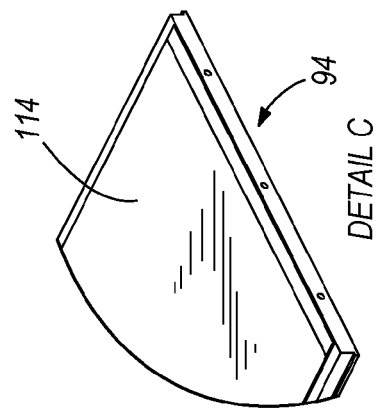
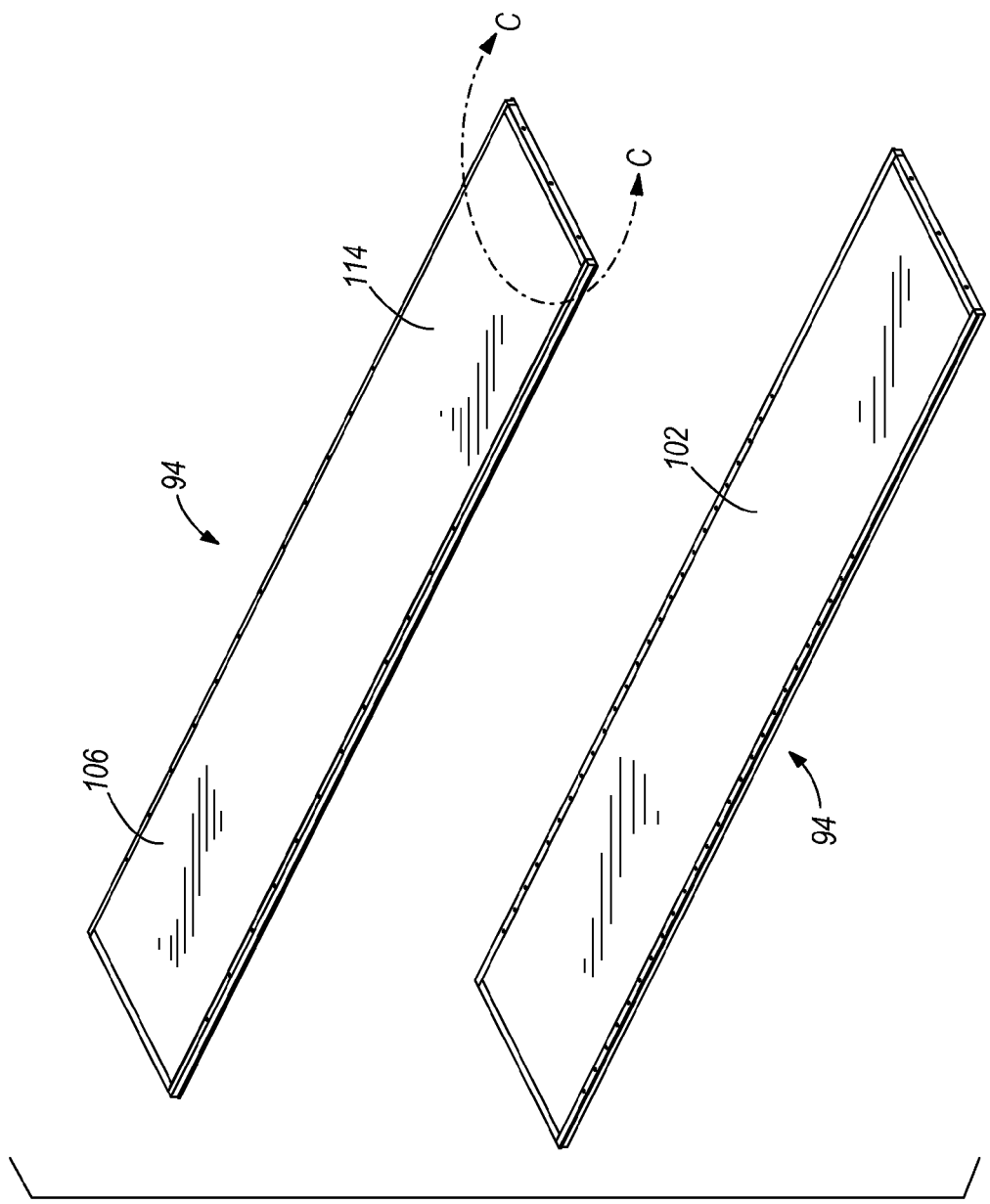
FIG. 5

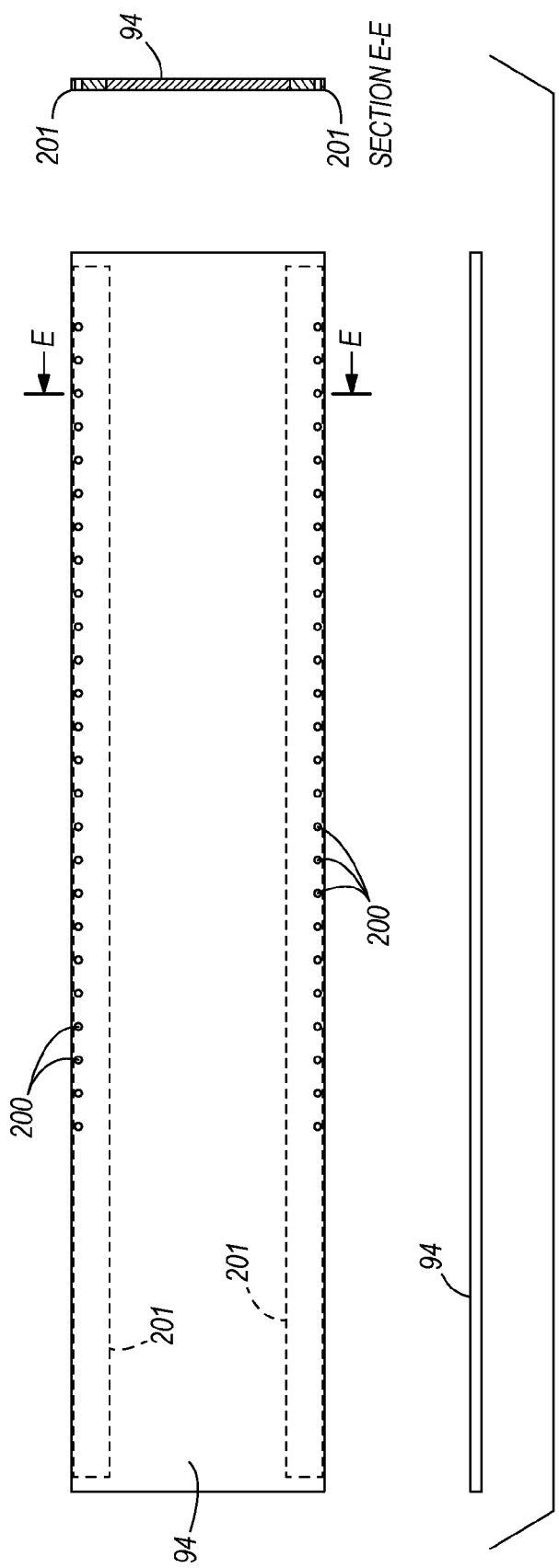
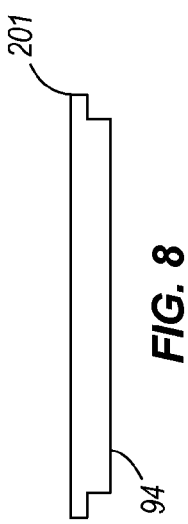
FIG. 7
FIG. 8

DETAIL N

DETAIL N

DETAIL N

SECTION Q-Q

DETAIL R

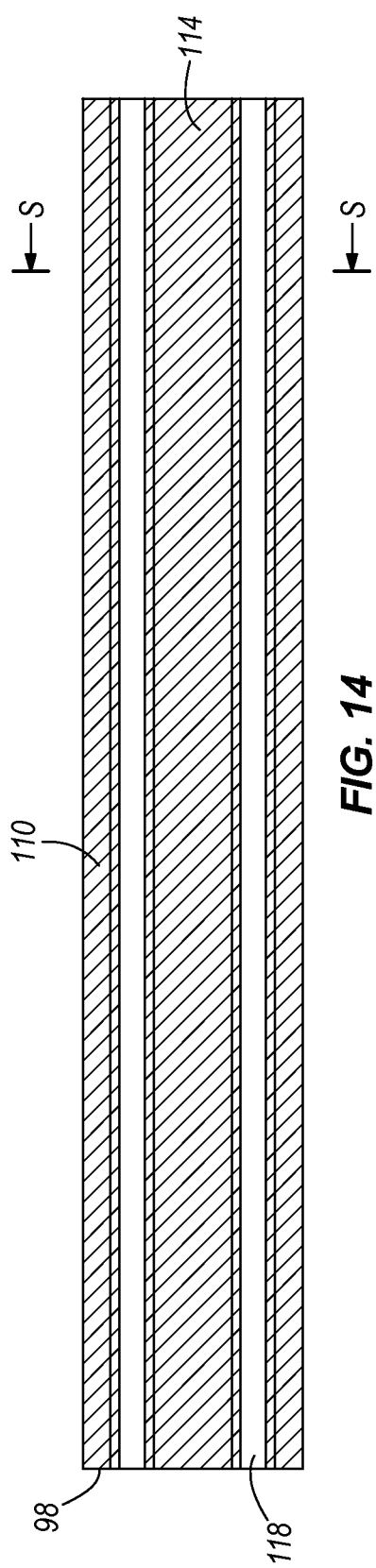
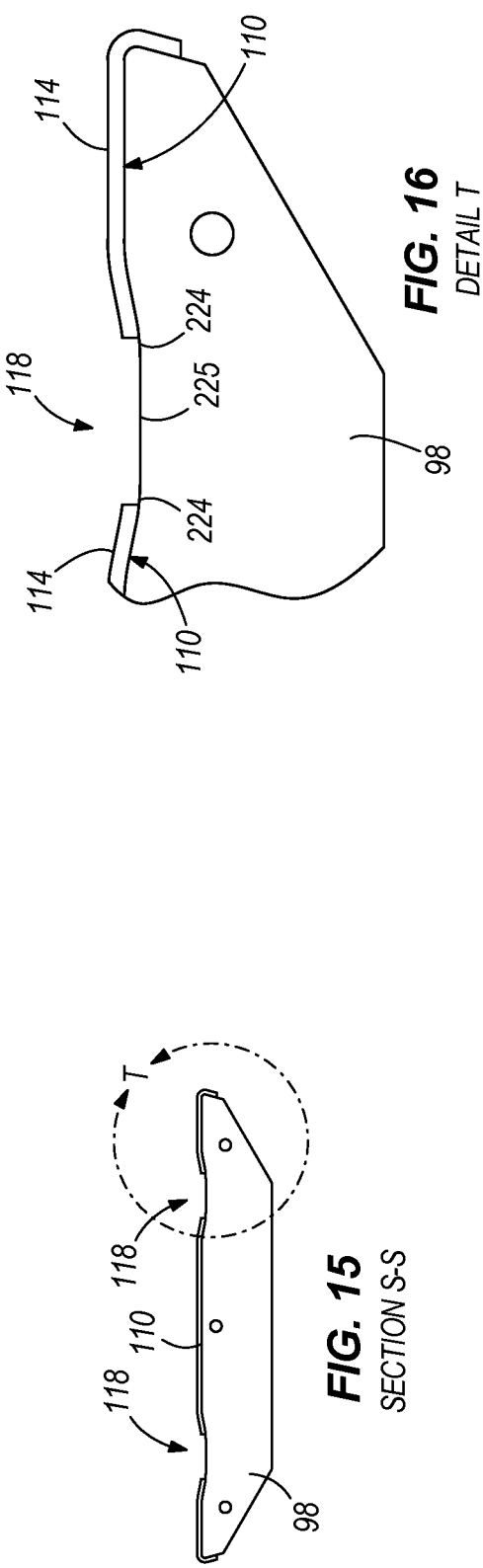

PATIENT SUPPORT DEVICE WITH LOW ATTENUATION PROPERTIES

RELATED APPLICATIONS

This application is a non-provisional application of and claims priority to U.S. Provisional Patent Application Ser. No. 61/246,927, filed on Sep. 29, 2009, the contents of which are incorporated herein by reference.

FIELD OF THE INVENTION

Embodiments of the invention relate to a radiation therapy imaging and treatment system. More specifically, embodiments of the invention relate to a patient support device having low attenuation properties and for use with a radiation therapy imaging and treatment system.

BACKGROUND OF THE INVENTION

Medical equipment for radiation therapy treats tumorous tissue with high energy radiation. The dose and the placement of the dose must be accurately controlled to insure both that the tumor receives sufficient radiation to be destroyed, and that damage to the surrounding and adjacent non-tumorous tissue is minimized. Intensity modulated radiation therapy ("IMRT") treats a patient with multiple rays of radiation each of which may be independently controlled in intensity and/or energy. The rays are directed from different angles about the patient and combine to provide a desired dose pattern. In external source radiation therapy, a radiation source external to the patient treats internal tumors. The external source is normally collimated to direct a beam only to the tumor location. Typically, the radiation source consists of either high-energy X-rays, electrons from certain linear accelerators, or gamma rays from highly focused radioisotopes.

One way to control the position of the radiation delivered to the patient is through the use of a patient support device, such as a couch, that is adjustable in one or more directions. Similar patient support devices are also used in computed tomography ("CT") scanning devices and Magnetic Resonances Imagers ("MRIs"). The patient support device allows the patient to be moved into and out of a field of radiation and in some cases, allows for adjustments of patient position during a radiation treatment session.

SUMMARY OF THE INVENTION

When a patient support device, such as a couch, is used in a radiation treatment therapy system, there are many variables that should to be accounted for. For example, the construction materials and the configuration of electronics used to operate the patient support device should be carefully selected to ensure smooth operation of the device and precise measurement of a device's position (when the device has multiple movable parts). When these features are adequately considered in a radiation environment, the patient support device can be a useful tool in improving treatment outcomes.

In some cases, the patient support device may utilize a multiple-piece table top assembly for supporting the patient during imaging and/or treatment. In those cases, the patient rests on an upper support portion, sometimes called a pallet, which is movable with respect to other portions of the support device. The pallet moves the patient into and out of the radiation beam. Since the pallet is moved into the beam path, the pallet may absorb, or attenuate, some of the radiation beam, thus potentially interfering with the imaging and/or treatment functions in various ways. It is optimal for the pallet to have a balance of strength and supportability, as well as minimal radiation attenuation properties. However, it is also desirable to use materials to construct the pallet and patient support device that have an adequate useful life when subjected to the radiation delivered by the radiation therapy treatment system.

Accordingly, embodiments of the invention provide a patient support device for a radiation therapy treatment system. The device includes a support having an upper surface and a lower surface and having a fixture hole configuration for receiving a patient fixation device. The fixture hole configuration includes at least one recess and reinforcing material positioned inside at least a portion of the at least one recess.

Embodiments of the invention also provide a method of manufacturing a patient support device for a radiation therapy treatment system. The method includes providing a support having a lower surface and an upper surface, and configuring the support to receive a patient fixation device by forming at least one recess in the lower surface of the support and inserting a reinforcing material into at least a portion of the interior of the at least one recess.

In addition, embodiments of the invention provide a patient support device for a radiation therapy treatment system. The device includes a support having an upper surface that includes at least one channel. Flat flex cable used to operate the patient support device is positioned within the at least one channel.

Other aspects of the invention will become apparent by consideration of the detailed description and accompanying drawings.

BRIEF DESCRIPTION OF THE DRAWINGS

FIG. 5 includes top and bottom perspective views of an upper support of the table assembly of FIG. 4.

FIG. 7 includes top and side views of an upper support of the table assembly of FIG. 4.

FIG. 8 is a side view of another upper support of the table assembly of FIG. 4.

FIG. 14 is a top view of the lower support of FIG. 10, illustrating a bearing layer.

FIG. 15 is an end view of the lower support of FIG. 11.

FIG. 16 is an exploded view of the lower support of FIG. 15, illustrating a bearing layer.

DETAILED DESCRIPTION

Figure 1:
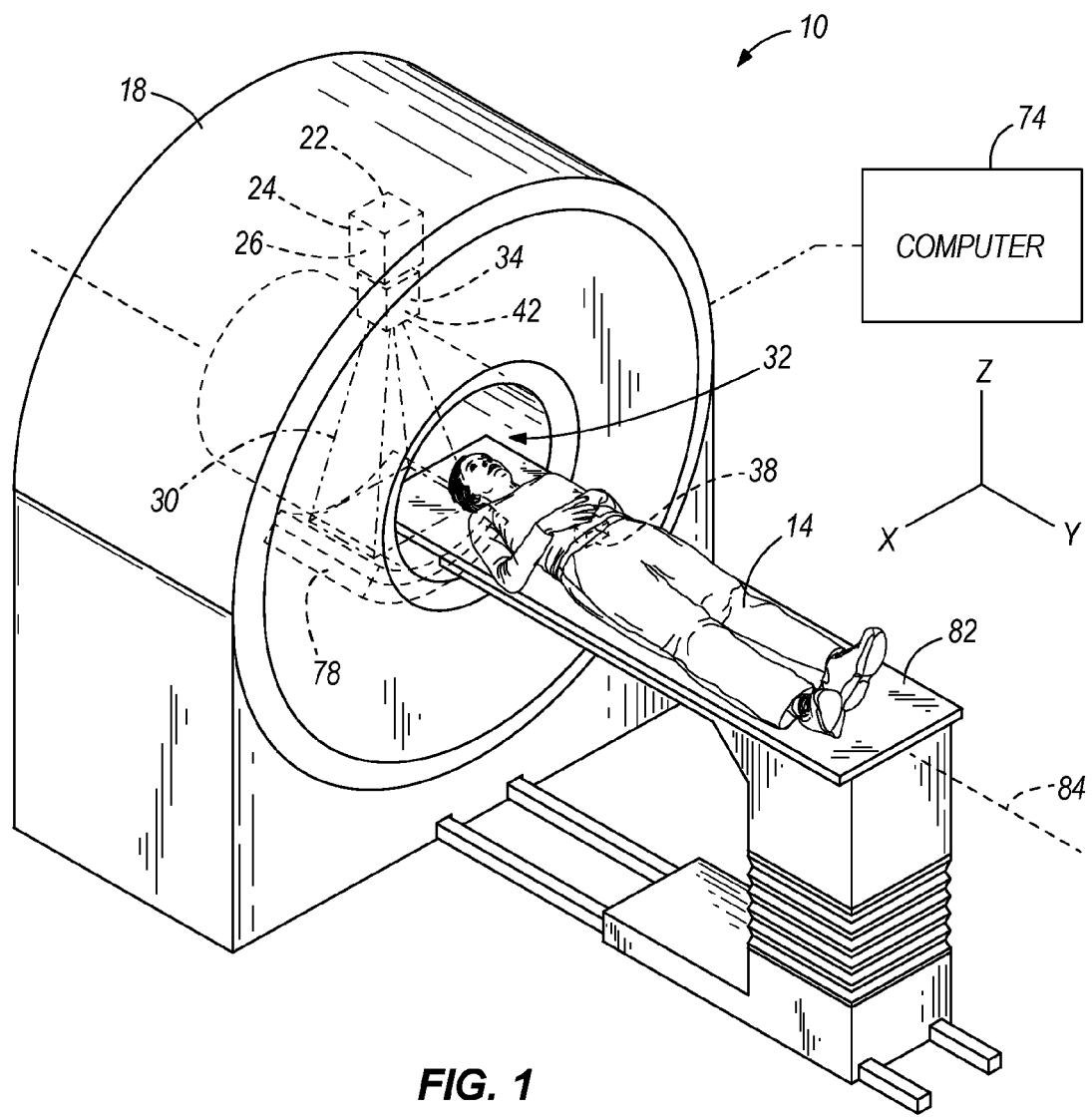
FIG. 1 is a perspective view of a radiation therapy treatment system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein are meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium). As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 according to one embodiment of the invention that provides radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 supports a radiation module 22, which includes a radiation source 24 and a linear accelerator 26 (a.k.a. "a linac") that generates a beam 30 of radiation. Although the gantry 18 shown in FIG. 1 is a ring gantry, i.e., it extends through a full 360° arc to create a complete ring or circle, other types of mounting arrangements may also be employed. For example, a C-type, partial ring gantry, or robotic arm gantry arrangement could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped. The gantry 18 of the illustrated embodiment defines a gantry aperture 32 into which the patient 14 moves during treatment.

The radiation module 22 also includes a modulation device 34 operable to modify or modulate the radiation beam 30. The modulation device 34 modulates the radiation beam 30 and directs the radiation beam 30 toward the patient 14. Specifically, the radiation beam 30 is directed toward a portion 38 of the patient 14. The portion 38 may include the patient's entire body, but is generally smaller than the patient's entire body and can be defined by a two-dimensional area and/or a three-dimensional volume. The portion 38 may include or be referred to as a target or target region or a region of risk. If the portion 38 includes a region at risk, the radiation beam 30 is preferably diverted from the region at risk. Such modulation is sometimes referred to as intensity modulated radiation therapy ("IMRT").

Figure 2:
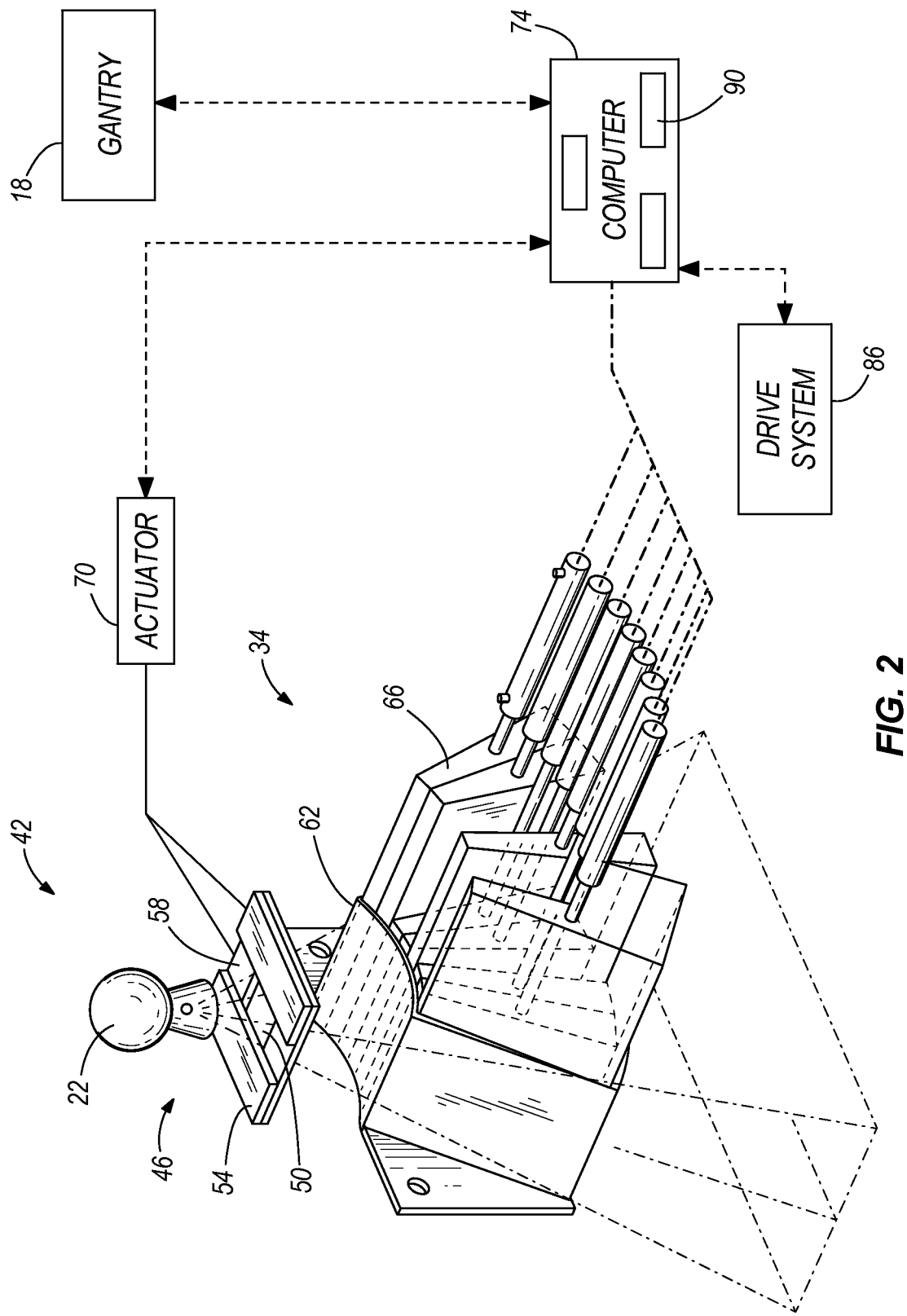
FIG. 2 is a perspective view of a multi-leaf collimator that can be used in the radiation therapy treatment system of FIG. 1.

The modulation device 34 includes a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50. The position of the jaws 46 regulates the shape of the beam 30 that is delivered to the patient 14.

In one embodiment, as illustrated in FIG. 2, the modulation device 34 comprises a multi-leaf collimator 62 (a.k.a. "MLC"), which includes a plurality of interlaced leaves 66 operable to move between multiple positions to modulate the intensity of the radiation beam 30. It is also noted that the leaves 66 can be moved to a position anywhere between a minimally and maximally-open position. The plurality of interlaced leaves 66 modulate the strength, size, and shape of the radiation beam 30 before the radiation beam 30 reaches the portion 38 on the patient 14. Each of the leaves 66 is independently controlled by an actuator 70, such as a motor or an air valve, so that the leaf 66 can open and close quickly to permit or block the passage of radiation. The actuators 70 can be controlled by a computer or controller 74.

The radiation therapy treatment system 10 can also include a detector 78 (e.g., a kilovoltage or a megavoltage detector) that receives the radiation beam 30, as illustrated in FIG. 1. The linear accelerator 26 and the detector 78 can also operate as a computed tomography ("CT") system to generate CT images of the patient 14. The linear accelerator 26 emits the radiation beam 30 toward the portion 38 of the patient 14. The portion 38 absorbs some of the radiation. The detector 78 detects or measures the amount of radiation absorbed by the portion 38. The detector 78 collects the absorption data from different angles as the linear accelerator 26 rotates around and emits radiation toward the patient 14. The collected absorption data is transmitted to the computer 74, and the computer 74 processes the collected adsorption data to generate images of the patient's body tissues and organs. The images can also illustrate bone, soft tissues, and blood vessels.

The system 10 can also include a patient support device, shown as a couch 82 in FIG. 1, to support at least a part of the patient 14 during treatment. For example, while the illustrated couch 82 is designed to support the patient's entire body, in other embodiments of the invention, the patient support device can be designed to support only a part of the patient 14 during treatment. The couch 82, or at least portions thereof, moves into and out of the field of radiation along an axis 84.

With reference to FIGS. 3-6, the couch 82 includes a table assembly 92 coupled to a base 93 via a platform 95. The table assembly 92 includes an upper support 94 movably coupled to a lower support 98. With particular reference to FIG. 5, the upper support 94 is a substantially flat, rectangular support member, sometimes also referred to as a pallet, on which the patient 14 is supported during treatment. The upper support 94 is movable with respect to the lower support 98 to move the patient 14 into and out of the radiation beam 30 during treatment. In the illustrated embodiment, the upper and lower supports 94, 98 are composed of a carbon fiber composite, although other suitable compositions of the supports are possible.

The upper support 94 has an upper surface 102 and a lower surface 106. The upper surface 102 includes a patient treatment area 104 and a fixation device area 105. The patient treatment area generally supports the patient 14 or a portion thereof. The fixation device area 105 extends around the perimeter of the patient treatment area 104 and, generally, does not directly support the patient 14 during a treatment session. For example, when positioned on the upper support 94, the patient 14 generally covers the patient treatment area 104 but does not cover the fixation device area 105. The fixation device area 105, however, receives patient fixation devices that hold the patient 14 in a generally fixed position during a treatment session.

The lower surface 106 of the upper support 94 contacts an upper surface 110 of the lower support 98. When the upper support 94 moves with respect to the lower support 98, any friction that builds up between the supports can interrupt the operation of the electronics that control the operation of the couch 82 and the operation of the system 10 in general. Further, when the supports 94 and 98 are composed of a carbon fiber composite, friction between the supports 94 and 98 can cause the creation and build-up of carbon dust, which can also cause problems with couch operation. Additionally, if the surfaces of the upper and lower supports 94, 98 contact each other directly, the contact results in additional wear and possible warping of the supports themselves, which may not only reduce the precision with which the couch can operate to position a patient, but may also cause couch failure. In view of these concerns, the lower surface 106 of the upper support 94 can include a bearing layer 114 (see FIGS. 4 and 5) that reduces friction between the lower surface 106 of the upper support 94 and the upper surface 110 of the lower support 98 when the upper support 94 is moved with respect to the lower support 98. The bearing layer 114 can include a polyimide laminate that is coupled to the lower surface 106 using a pressure sensitive adhesive. For example, in some embodiments, the laminate is Kapton™, available from DuPont. Alternatively or in addition, the bearing layer 114 can be included in the upper surface 110 of the lower support 98.

Figure 4:
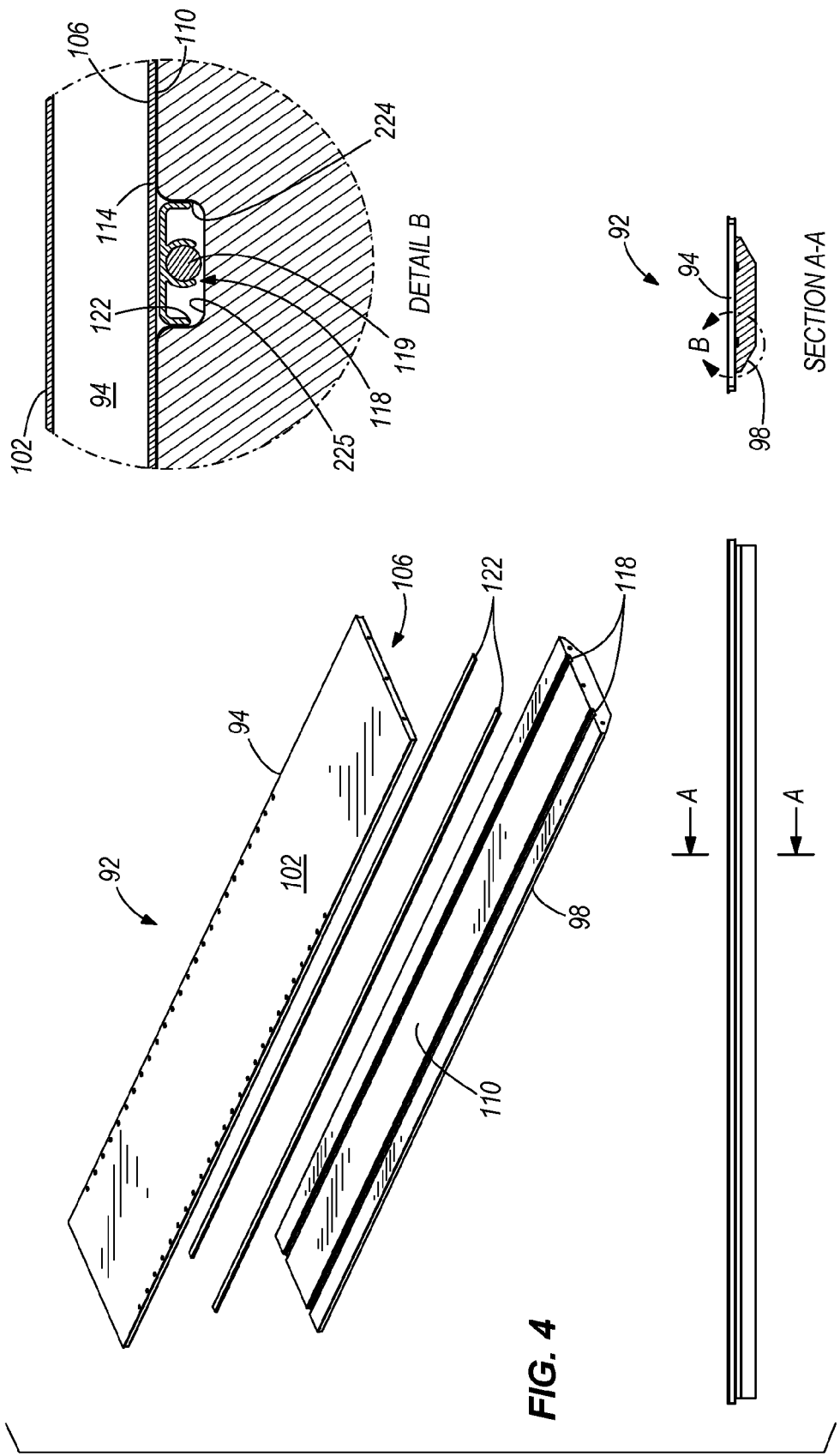
FIG. 4 includes exploded and side views of a table assembly of the patient support device of FIG. 3.
Figure 6:
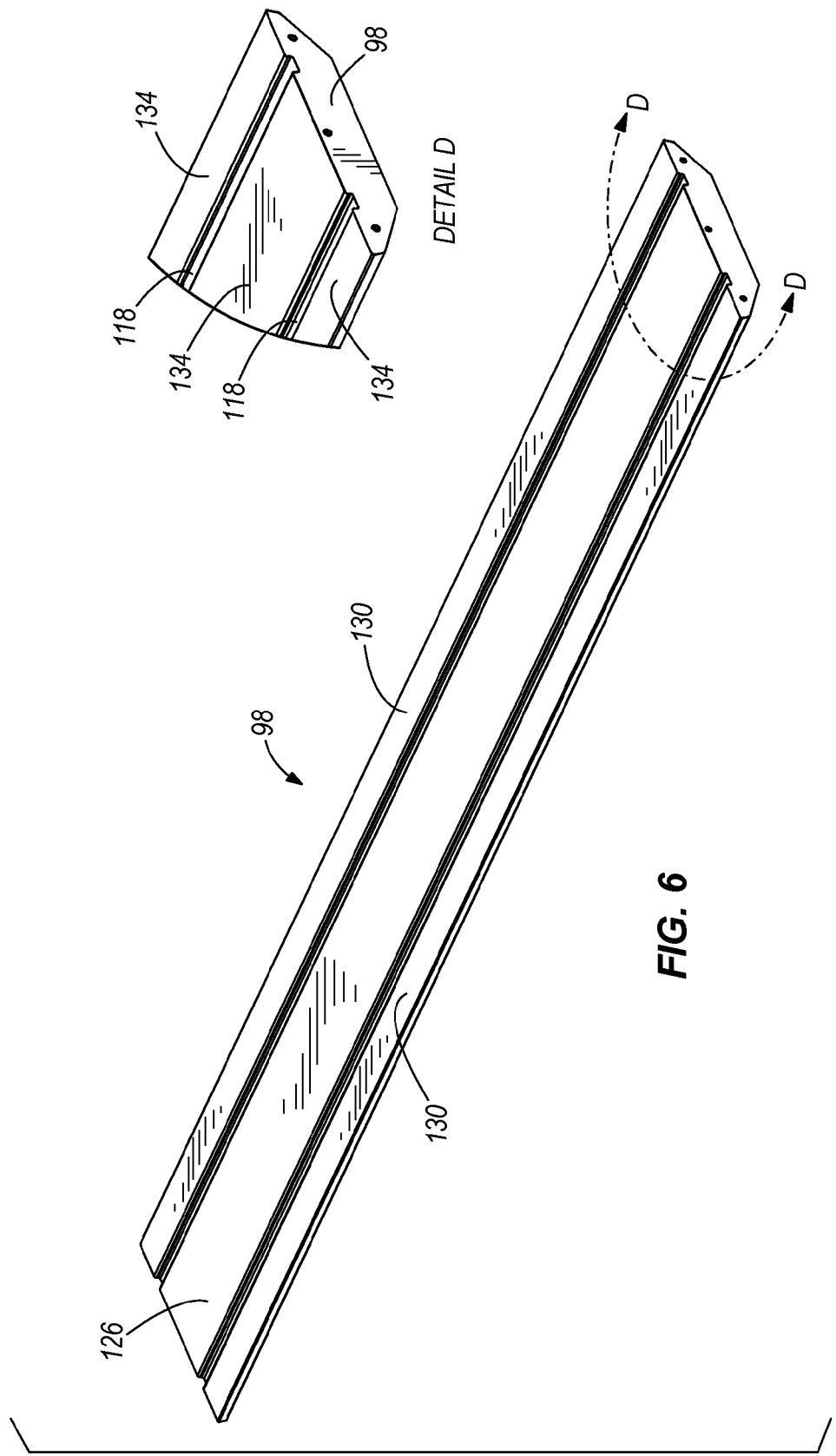
FIG. 6 is a perspective view of a lower support of the table assembly of FIG. 4.

With continued reference to FIG. 4, the lower support 98 includes two channels 118 that receive and house wiring 119 used to operate the couch 82. The two channels 118 can be designed to hold the wiring 119 in a straight and constant position for image reproducibility. In addition, as shown in FIG. 4, a retaining member 122 can be used to hold the wiring 119 in place. The retaining member 122 and/or the outer sheathing of the wiring 119 itself can be composed of radiation resistant material to protect the wiring 119 in the high radiation environment of the couch 82 and ensure proper functioning. The spacing and design of the channels 118 separates the power lines from the data lines included in the wiring 119 to prevent interference problems that occur when the two lines are not sufficiently spaced.

The couch 82 is movable in the X, Y, and Z directions, as illustrated in FIG. 1. Positioning of the couch 82, and thus the positioning of the patient 14, with respect to the gantry 18 and the radiation beam 30 must be precise to ensure that the radiation is delivered to the proper portion(s) of the patient 14. The movement of the couch 82 can be controlled by a couch operator using a control keypad 140 (see FIG. 3), and, in some embodiments, certain aspects of couch movement are controlled automatically by the system 10.

Figure 3:
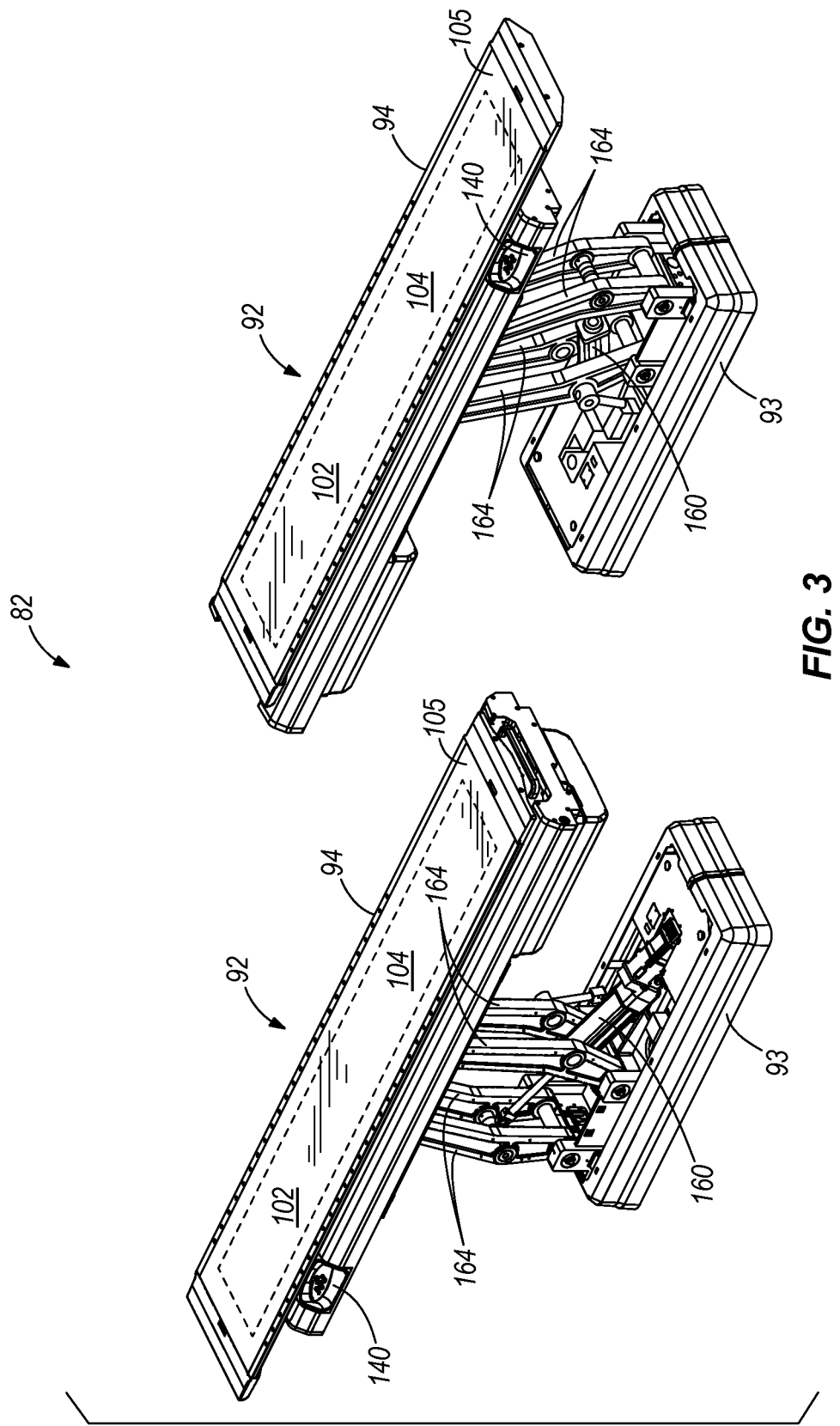
FIG. 3 includes perspective views of a patient support device for use with the system of FIG. 1.

As shown in FIG. 3, the couch 82 also includes support arms 164 that couple the table assembly 92 to a riser 168 of the base 93. The couch 82 can include two pairs of support arms 164, with each arm 164 within a pair of arms being parallel to the other arm. As the table assembly 92 is raised and lowered, a longitudinal axis of each arm 164 within a pair remains parallel to the other arm 164, and a plane $P_1$ formed by the longitudinal axes of one pair of arms 164 does not intersect a plane $P_2$ formed by the longitudinal axis of the other pair of arms.

Another aspect to account for during radiation therapy of a patient 14 on the couch 82 is attenuation. When an object is placed in the path of the radiation beam 30, such as the upper support 94, unless the object is made of a radiotransparent material, the object will attenuate (i.e., absorb) some portion of the radiation beam 30. This attenuation must be reduced, eliminated, and/or accounted for to properly deliver a desired dose to the patient 14. In some embodiments, software operating the system 10 obtains information (e.g., via feedback loops and other inputs) about the positioning of the couch 82 that it uses to account for certain properties of the couch 82. For example, the software can warn an operator when the couch 82 has changed locations. However, most systems 10 have limited ability to accurately account for beam attenuation through a patient support.

The fewer the treatment beams used to treat the patient 14, such as a fixed beam treatment delivery, the more important it is to reduce, eliminate, or account for radiation attenuation. In particular, with fewer beams it is more important to account for the exact impact each beam will have on the patient and it is more likely that a given beam will travel through portions of the couch 82, such as the upper support 94. Also, some types of radiation therapy, such as electron beam therapy, may be more susceptible to attenuation effects. Furthermore, as described below, in some embodiments, the upper support 94 is reinforced to provide structural integrity so that it does not flex, warp, or twist under the load of the patient 14 and to provide adequate support for fixation devices attached to the couch 82 that hold the patient 14 in a generally fixed position. The additional material used to reinforce the upper support 94, however, can cause additional imaging artifacts.

For example, as illustrated in FIG. 7, known upper supports 94 include fixture holes 200 sized and placed so that fixation devices can be attached to the upper support 94 to assist in positioning a patient. Known upper supports 94 also commonly include one or more support members 201, such as a rod or bar (see FIG. 7) or a lip (see FIG. 8). The support members 201 can be formed of phenolic materials, plastics, metals, or other low-density hardened materials. The support members 201 are commonly constructed within the upper support 94 to enhance the support properties of the upper support 94 adjacent the fixture holes 200. For example, the support member 201 can extend the length of the upper support 94 adjacent to the fixture holes 200, and, in some embodiments, as shown in FIG. 7, the fixture holes 200 can be drilled through a portion of the support member 201. However, although the support members 201 provide additional structural integrity to the upper support 94, the support members 201 cause high radiation attenuation. In particular, if a patient treatment plan calls for radiation beams to pass through a support member 201 prior to reaching a portion of a patient, the resulting attenuation caused by the support member 201 must be carefully accounted for otherwise the patient will not receive the proper amount of radiation.

Figure 9:
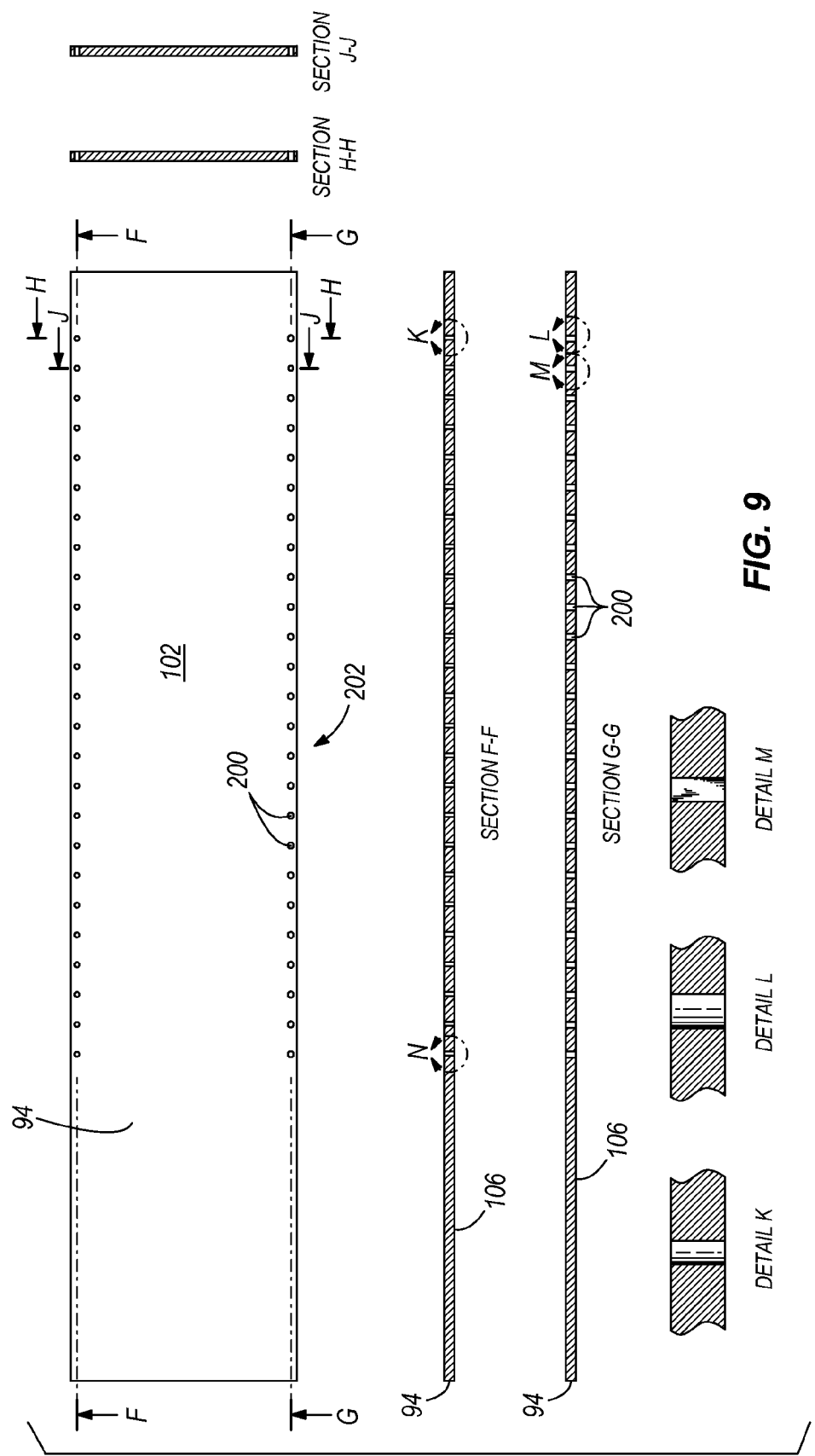
FIG. 9 includes top and cross-sectional views of an upper support of a table assembly according one embodiment of the present invention.

Accordingly, embodiments of the present invention provide upper supports and methods of manufacturing the same having the desired structural integrity and the reduced overall radiation attenuation properties without requiring an internal support bar or additional support members added to the outer edges of the upper support 94. In particular, FIG. 9 illustrates an upper support 94 according to one embodiment of the invention. The upper support 94 includes a fixture support configuration 202 that includes one or more fixture recesses or holes 200 sized and placed so that fixation devices can be attached to the upper support 94 to assist in positioning the patient 14 on the couch 82. As shown in FIG. 9, the fixture holes 200 are positioned along the outer edges of the upper support 94. It should be understood, however, that the fixture holes 200 can be positioned at any location(s) and in any pattern on the upper support 94. The fixture holes 200 can have varying diameters. In some embodiments, the fixture holes 200 have diameters ranging from approximately ten millimeters (see Detail K and Detail M) to approximately twelve millimeters (see Detail L). However, it should be understood that the fixture holes 200 can be constructed with any diameter necessary to receive and support a fixation device. In addition, the fixture holes 200 can be constructed in varying shapes, such as cylindrical holes (see Detail K and Detail L) or rectangular slots (see Detail M). It should also be understood that the fixture holes 200 included on a particular upper support 94 can be generally identical or can be varied in shape, size, or position on the upper support 94.

The upper support 94 is generally crafted of carbon fiber composite materials or by other known construction materials and methods. To add structural integrity to the upper support 64, the fixture holes 200 include a reinforced portion around at least a portion of their internal perimeter. For example, rather than adding support members 201 within the upper support 94 (as shown in FIGS. 7 and 8), the fixture holes 200 are construed such that each fixture hole 200 includes a portion of reinforcing material different than the material of the upper support 94. The material and configuration of the reinforcing portion provides structural integrity to the support 64 and, in some embodiments, also have low attenuation properties.

Figure 9A:
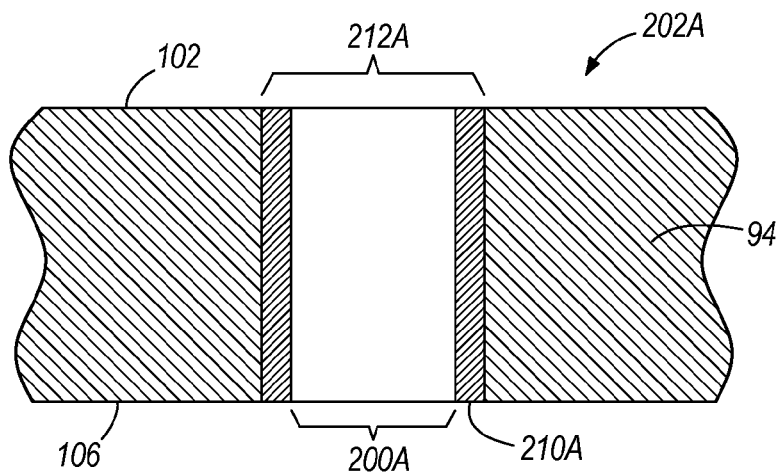
FIG. 9A is a cross-sectional view of a fixture hole configuration for the upper support of FIG. 8 according to one embodiment of the invention.

As shown in FIG. 9A, in one embodiment, the fixture support configuration 202A includes fixture recesses or holes 200A that include a thin wall 210A of hardened viscous material, such as a low attenuating epoxy, around their inner perimeter. To create the fixture holes 200A, holes or recesses 212A are machined drilled up through the lower surface 106 (under or bottom side) of the upper support member 94. In some embodiments, the holes 212A are drilled up to but not through the upper surface 102 of the upper support 94. In other embodiments, as shown in FIG. 9A, the holes 212A are drilled up to and through the upper surface 102.

Each hole 212A is spaced on the upper support 94 to accept a desired patient fixation device but is sized an amount larger than what will ultimately be needed to secure the patient fixation devices. For example, the holes 212A can be drilled approximately one millimeter larger than the size ultimately needed to secure the patient fixation devices. The holes 212A are then filled with the viscous material, such as an epoxy. In some embodiments, the holes 212A are filled with the viscous material within one millimeter of the lower surface 106 of the upper support 94.

After the viscous material has cured and hardened, the holes 200A are machine drilled down from the upper surface 102 (top side) of the upper support 94 and through the hardened viscous material. The edges of the holes 200A can also be chamfered. The holes 200A are sized to receive the fixation devices. For example, as noted above, the holes 200A can be have a diameter from approximately ten millimeters to approximately twelve millimeters. In some embodiments, the size of the holes 200A can be calculated on a case by case basis, depending on the appropriate size of the ultimate hole needed to receive the fixture devices. In general, the thickness of the reinforcing wall 210 left around the inside perimeter of the holes 200A should be minimized to minimize attenuation while still providing adequate structural support. In some embodiments, the wall 210A of hardened viscous material is approximately one-half of a millimeter thick.

Because the holes 200A are generally smaller than the holes 212A, the thin wall 210A of hardened viscous material is left along the depth of the inside perimeter of the holes 200A and increases the overall structural integrity of the upper support 94. Furthermore, the reinforced holes 200A give the upper support 94 a lower cross-sectional density and, consequently, a lower radiation attenuation than conventional upper supports that include additional integrated support members 201 (see FIGS. 7 and 8). The thin wall 210A of hardened viscous material can also seal off the material of the upper support 94, which allows for bio-cleaning capability.

Figure 9B:
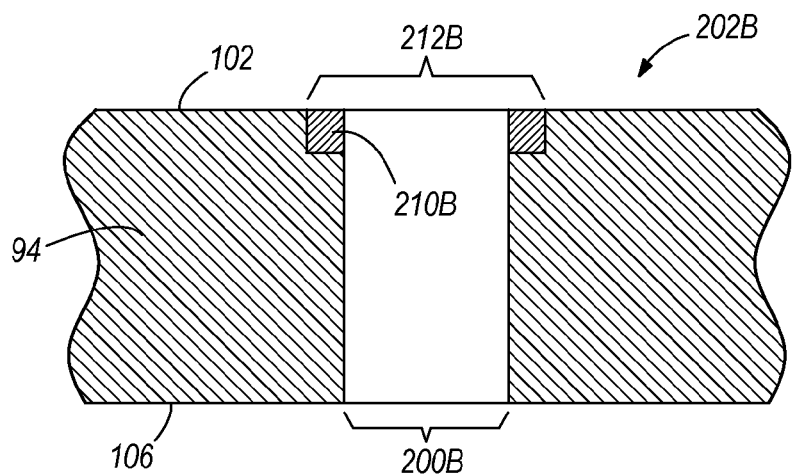
FIG. 9B is a cross-sectional view of a fixture hole configuration for the upper support of FIG. 8 according to another embodiment of the invention.

In an alternate embodiment, as illustrated in FIG. 9B, the upper support 94 includes a fixture support configuration 202B including one or more fixture recesses or holes 200B sized and spaced appropriately to receive the patient fixation devices. Each fixture hole 200B includes a washer 210B positioned around at least a portion of its inner perimeter. To create the fixture holes 200B, the holes or recesses 200B are machined drilled through the upper support 94. The holes 200B can be drilled up through the lower surface 106 of the upper support 94 or drilled down through the upper surface 102 of the upper support 94. As shown in FIG. 9B, in some embodiments, the holes 200B are drilled through the entire depth of the upper support 94.

Either prior to drilling the holes 200B completely through the upper support 94, or after drilling the holes 200B, a counter bore 212B is drilled in the upper portion of each hole 200B that is sized to accept the washer 210B. The outer diameter of the washer 210B can be approximately the same as the diameter of the counter bore 212B, and the inner diameter of the washer 210B can be approximately the same as the diameter of the hole 200B. The washer 210B, which may be made of plastic or a similar low attenuating material, is inserted into the counter bore 212B to provide the desired support for attaching the fixation devices. The washer 210B can be press fit inside the counter bore 212B or adhered to the inner surface of the counter bore 212B and/or the hole 200B. It should be understood that although the washer 210B is illustrated in FIG. 9B around the upper portion of each hole 200B, the counter bore 212B and washer 210B could also be placed on the lower portion of each hole 200B. However, reinforced support around the upper portion of the hole 200B is more integral to the stability of the upper support 94. It should also be understood that the washer 210B can constructed in various shapes, including cylindrical shapes, polygon shapes, curved planar shapes, and horseshoe shapes.

Figure 9C:
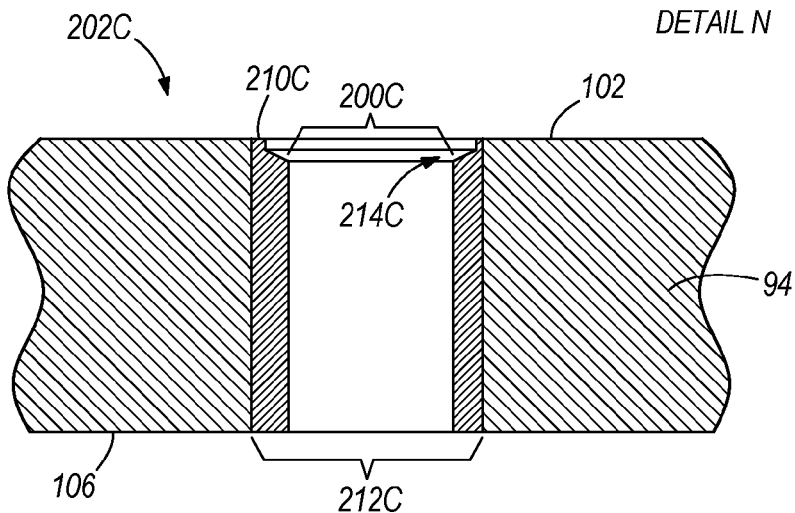
FIG. 9C is a cross-sectional view of a fixture hole configuration for the upper support of FIG. 8 according to yet another embodiment of the invention.
Figure 10:
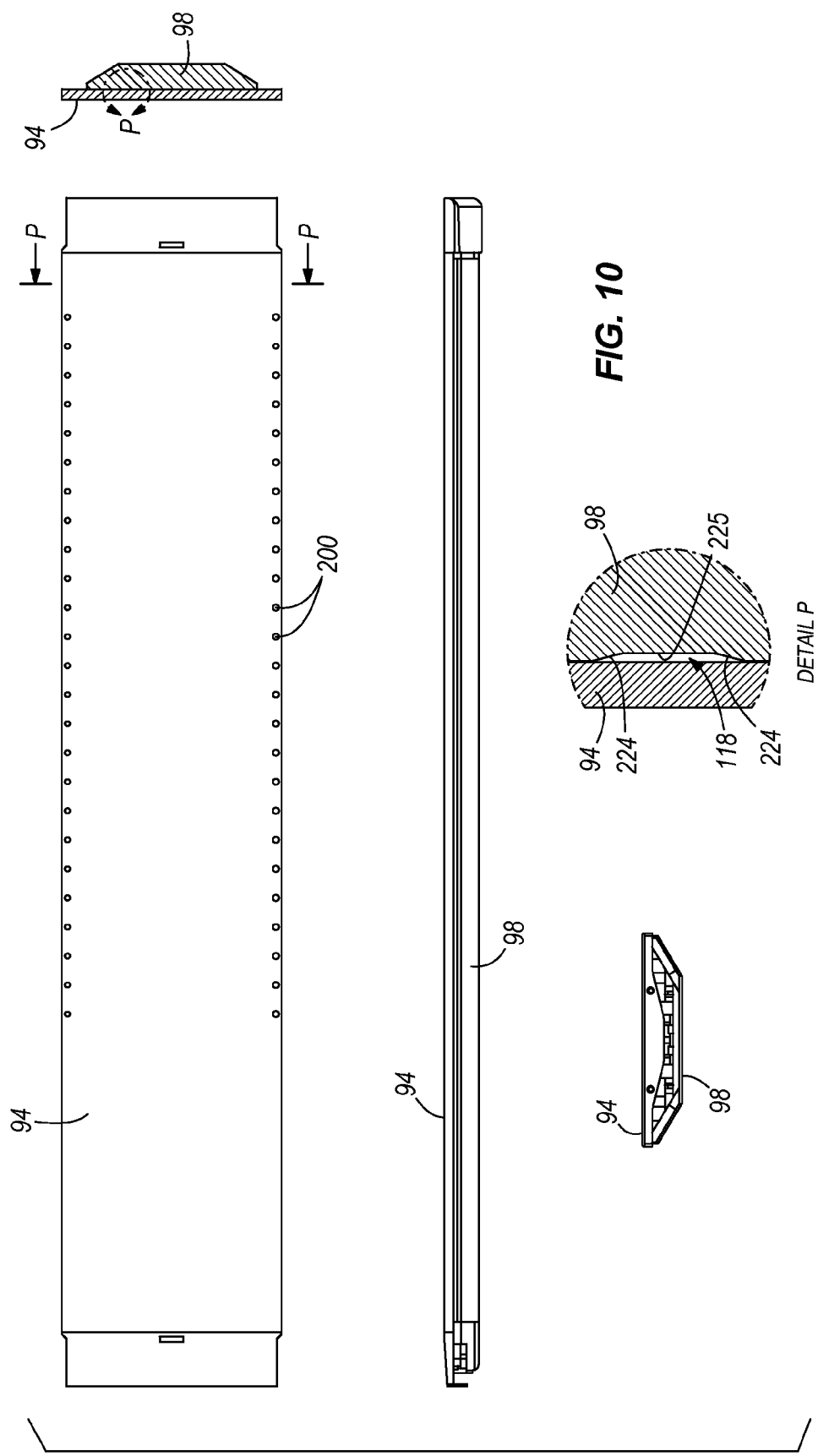
FIG. 10 includes top and side views of upper and lower support members for a table assembly according one embodiment of the invention.
Figure 11:
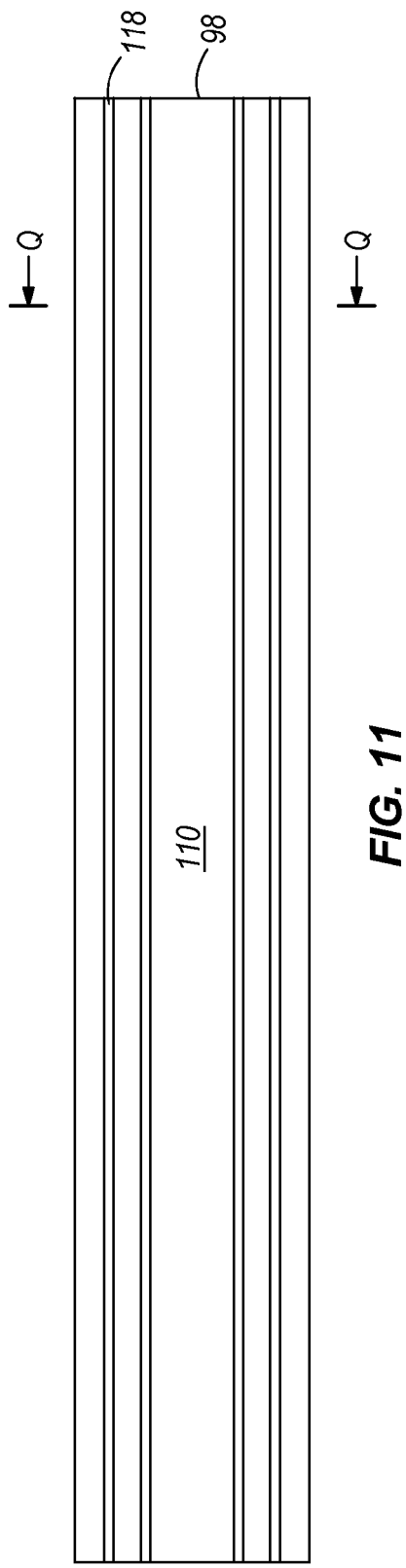
FIG. 11 is a top view of the lower support of FIG. 10.

In yet another embodiment, as illustrated in FIG. 9C, the upper support 94 includes a fixture support configuration 202C that includes one or more fixture recesses or holes 200C sized and spaced appropriately to receive the patient fixation devices. Each fixture hole 200C also includes an insert or sleeve 210C positioned around at least a portion of its inner perimeter. To create the fixture holes 200C, holes or recesses 212C are first machined drilled through the upper support 94. The holes 212C can be drilled up through the lower surface 106 of the upper support or drilled down through the upper surface 102 of the upper support. As shown in FIG. 9C, in some embodiments, the holes 212C are drilled through the entire depth of the upper support 94.

The holes 212C are spaced appropriately to receive the patient fixation devices but are sized an amount larger than necessary to accept the patient fixation devices. The sleeve 210C is then inserted in the each hole 212C, leaving the holes 200C that each have an inner diameter that is sized for receiving the patient fixation devices. The sleeve 210C may be constructed of carbon fiber material, plastic, Kapton™, or other low attenuating hardened materials. The sleeve 210C may be press fit or adhered to the inner surface of the holes 212C in any number of known manufacturing methods, such as using an epoxy or bounding agent. The general mathematical formula considered to minimize the attenuation with respect to the relative thickness of the material used for the sleeve 210C is as follows:

$$Chord_{Max} = \sqrt{D_{Outer}^2 - D_{Inner}^2}$$
$$= 2 \cdot \sqrt{R_{Outer}^2 - R_{Inner}^2}$$

The sleeve 210C can have various shapes. For example, the sleeve 210C can have a cylindrical shape, a polygon shape (e.g., a pentagon or hexagon shape), a curved planar shape, or a horseshoe shape. The sleeve 210C can cover the entire inner perimeter of the holes 212C or only a portion thereof. In addition, the sleeve 210C can have a thickness similar to the thin wall 210A of hardened viscous material described above with respect to FIG. 9A. In particular, the sleeve 210C can have a thickness of approximately one-half of a millimeter. As shown in FIG. 9C, in some embodiments, the sleeve 210c can include a tapered or recessed portion 214C. The tapered portion 214C can be designed to receive a particular fixation device and/or may be designed to reduce attenuation caused by the sleeve 210C by eliminating a sharp perpendicular edge.

In some embodiments, the sleeve 210C is removable to allow the sleeve 210C to be replaced or changed. For example, a user may remove the insert 210C and insert a new sleeve 210C that has a different shape, size, or material than the removed sleeve 210C. This feature allows users to modify the shape, size, or properties of the hole 200C based on the particular patient fixation devices being used with the couch 82. To allow a user to replace the sleeve 210C, the sleeve 210C and/or the upper support 94 can include a mechanism for selectively mounting the sleeve 210C, such as a lip, a notch, a tongue and groove, a clip, a replaceable adhesive, etc.

In yet another embodiment, the upper support 94 alone may provide the desired support properties without adding any additional support around the fixture holes 200 as described in the above embodiments. However, because the upper support 94 may comprise a material, such as foam or similar material, the material may flake or chip under the stress of repeated insertions and removals of the patient fixation devices. This flaking or chipping over time may stress the upper support 94 and cause the upper support 94 to lose the desired structural integrity. In such cases, instead of forming the fixture holes 200 in the upper support 94 via traditional mechanical drilling methods, such as using a drill bit, the holes 200 may be formed via laser drilling or other heated drilling mechanisms that essentially melt the core material of the upper support 94 around the perimeter of the hole 200. This method prevents the flaking and chipping by forming a hard surface against which the patient fixation devices interact with the upper support 94 without adding any additional material to the upper support 94 that may further increase the radiation attenuation properties of the upper support 94. Laser drilling and other heated drilling mechanisms can also be used to drill the various holes described above with respect to FIGS. 9A-9C.

Similar to the attenuation problems associated with support members 201 described above with respect to FIGS. 7 and 8, the channels 118 in the lower support 98 also raise attenuation issues. In particular, as described above with respect to FIG. 4, the channels 118 receive the wiring 119 that is used to operate the couch 82. As shown in FIG. 4, the channels 118 can be sized and spaced to receive standard cable-type wiring that includes bundles of wires in a generally circular shape housed within a radiation resistant housing. Accordingly, the channels 118 of known lower support 98 are U-shaped, with 90 degree corners and vertical walls. However, this configuration can severely attenuate a radiation beam 30. In particular, the 90 degree angles between the sidewalls 224 and the bottom wall 225 of the channel 118 and the straight, vertical sidewalls 224 attenuate the radiation beam 30 and/or cause radiation "shadows." A radiation shadow occurs when a beam 30 that is aimed directly at the patient 14 travels along the length of the sidewall 224 where it is subjected to the greatest attenuation and, consequently, has the maximum disruptive affect on the patient's treatment. In addition, given uncertainties from fraction to fraction in where precisely the patient will be positioned on the upper support 94, it is difficult to account for these shadows and attenuation of the beam in the treatment planning process. Thus, the more desirable solution is to reduce or eliminate the attenuation issue.

Figure 12:
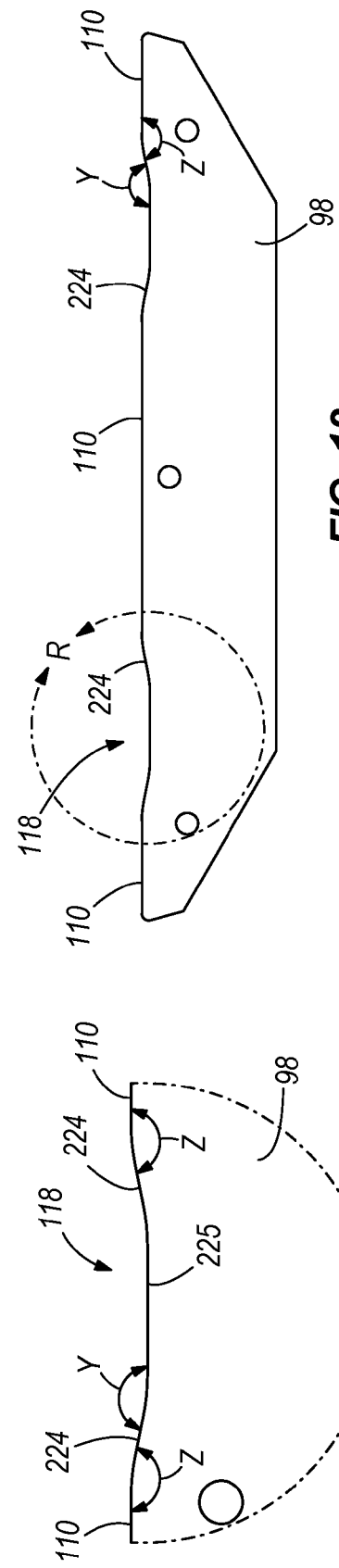
FIG. 12 is an end view of the lower support of FIG. 10, illustrating channels.
Figure 13:
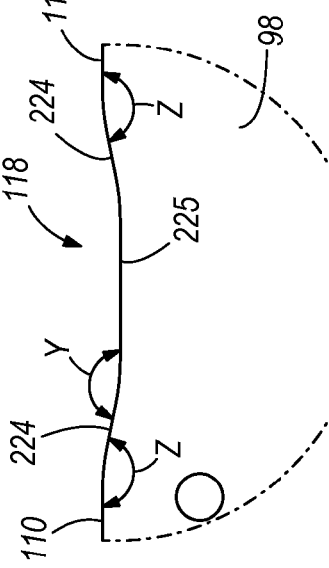
FIG. 13 is an exploded view of the channel of FIG. 12.

To address these attenuation issues, FIGS. 10-17 illustrate flattened, shallow channels 118 according to one embodiment of the invention. The channels 118 reduce attenuation by extending the angle Y between the sidewalls 224 of the channel 118 and a bottom 225 of the channel 118 from 90 degrees with respect to the bottom 225 to an obtuse angle with respect to the bottom 225 (see FIGS. 11-13). A mathematical formula can be used to optimize the angle Y, although in general, the more obtuse the angle Y (i.e., the flatter the sidewalls 224 of the channel 118 are with respect to the bottom 225 of the channel 118), the less attenuation and shadow effects. In addition, the angle of the sidewalls 224 with respect to the bottom 225 is chosen, in part, to eliminate the sharp angle (e.g., 90 degree angle) where the top of a sidewall 224 meets the upper surface 110 of the lower support 98, which acts as another attenuation hot spot. For example, as shown in FIGS. 12 and 13, the top angle Z is substantially obtuse with respect to the upper surface 110 of the lower support 98 and the sidewall 224. In general, keeping the profile of the channel 188 as rounded as possible (i.e., by removing vertical sections and sharp corners) minimizes the path length for any beam angle that passes through the lower support 98 and, consequently, minimizes beam attenuation. In one embodiment, the obtuse angle is approximately 170 degrees. However, in other embodiments, the obtuse angle can be from approximately 135 degrees to approximately 179 degrees.

As shown in FIGS. 14-16, the lower support 98 can also include a bearing layer 114. As described above with respect to FIG. 4, the bearing layer 114 reduces friction between the lower surface 106 of the upper support 94 and the upper surface 110 of the lower support 98 when the upper support 94 is moved with respect to the lower support 98. The bearing layer 114 can be constructed as strips or with openings that match the configuration of the channels 118. For example, as shown in FIG. 16, the bearing layer 114 is aligned with the top edge of each channel 118. In some embodiments, the bearing layer 114 can be tapered to match and align with the flattened sidewalls 224 as they reach the upper surface 110 of the lower support 98. Tapering the bearing 114 can also reduce the sharp edges on the lower support 98 that can cause high attenuation.

Even with the removal of the vertical walls and the 90 degree angles of the channels 118 that can cause severe attenuation, some attenuation may still occur when a radiation beam 30 is directly aligned with the channel sidewall 224, regardless how shallow the channel 118 is. However, another benefit of the shallow or flattened channel configuration is that the beams that are attenuated are at such an angle with respect to the patient's position on the couch 82 that the attenuated beams will be cast substantially outside the patient treatment area 104 such that they miss the patient 14 and thus do not impact the patient's treatment or cause attenuation shadow effects. Therefore, the flatten channel configuration illustrated in FIGS. 11-16 casts attenuated beams away from (i.e., to miss intersecting with) the patient 14.

As described above, in known couch assemblies, the wiring 119 used to operate the couch 82 is placed along the length of the couch 82 within the channels 118, and the wiring 119 is bundled together in a circular-shape cable-type configuration (see FIG. 4). However, standard cable-type wiring with its thick circular-shape and radiation resistant housing causes additional attenuation issues. To address this attenuation issue, embodiments of the present invention use flattened wiring 230, such as flat flex cable that includes wiring in a flexible printed circuit board configuration. As compared to thicker, circular-shaped wiring 119, the flattened wiring 230 is much thinner and less attenuating while still safely handling the current required by the couch 82 components. As such, although the flattened cable 230 may create more surface area of potentially attenuating material, the thinner design of the flattened cable 230 attenuates a beam at any given point must less than the thicker, circular wiring 119. Therefore, the overall attenuation effect caused by the flattened cable 230 is lower than the attenuation effects caused by the thicker, circular-shaped wiring 119.

Figure 17:
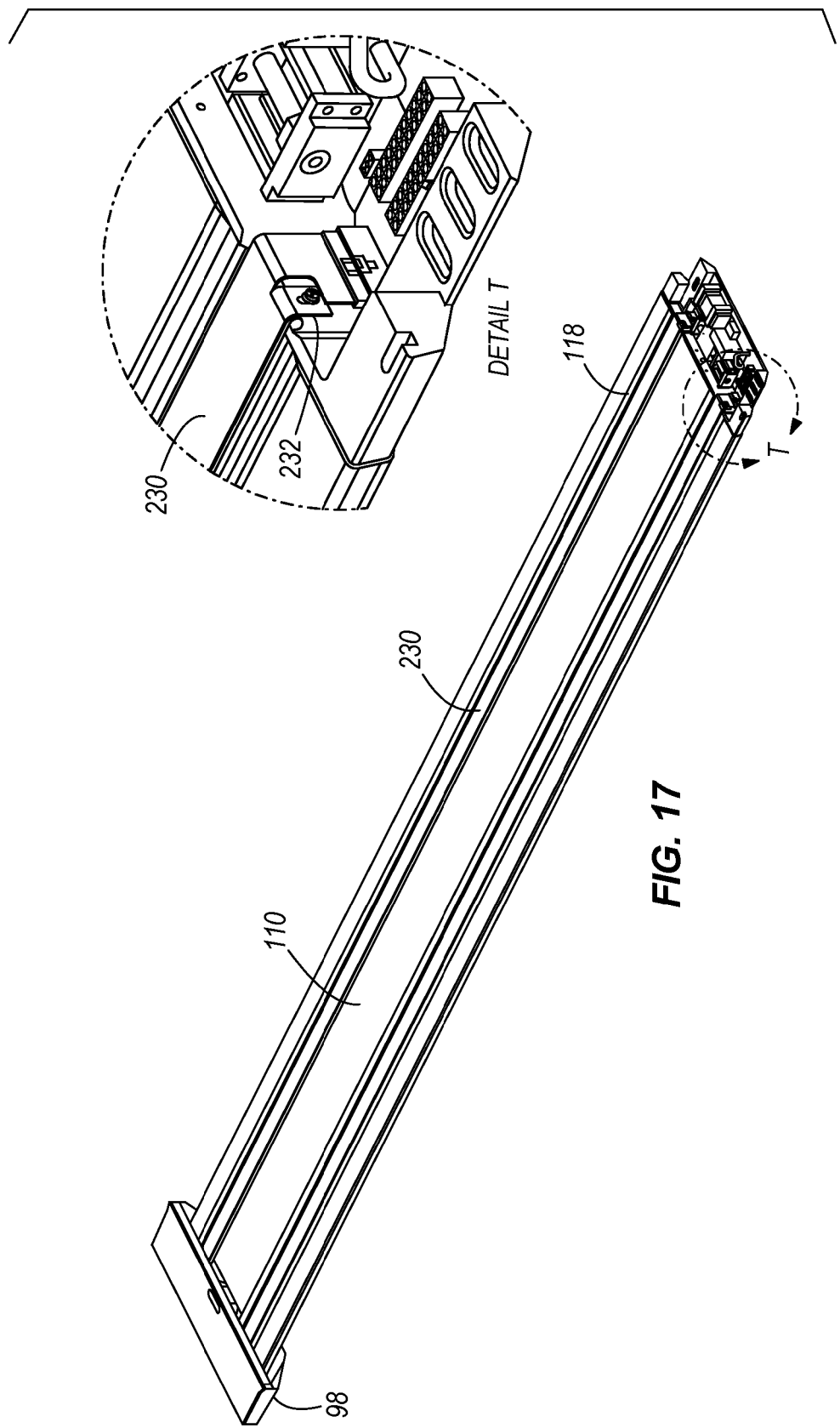
FIG. 17 is a perspective view of the lower support of FIG. 11, illustrating receptacles for flattened wiring.
Figure 18:
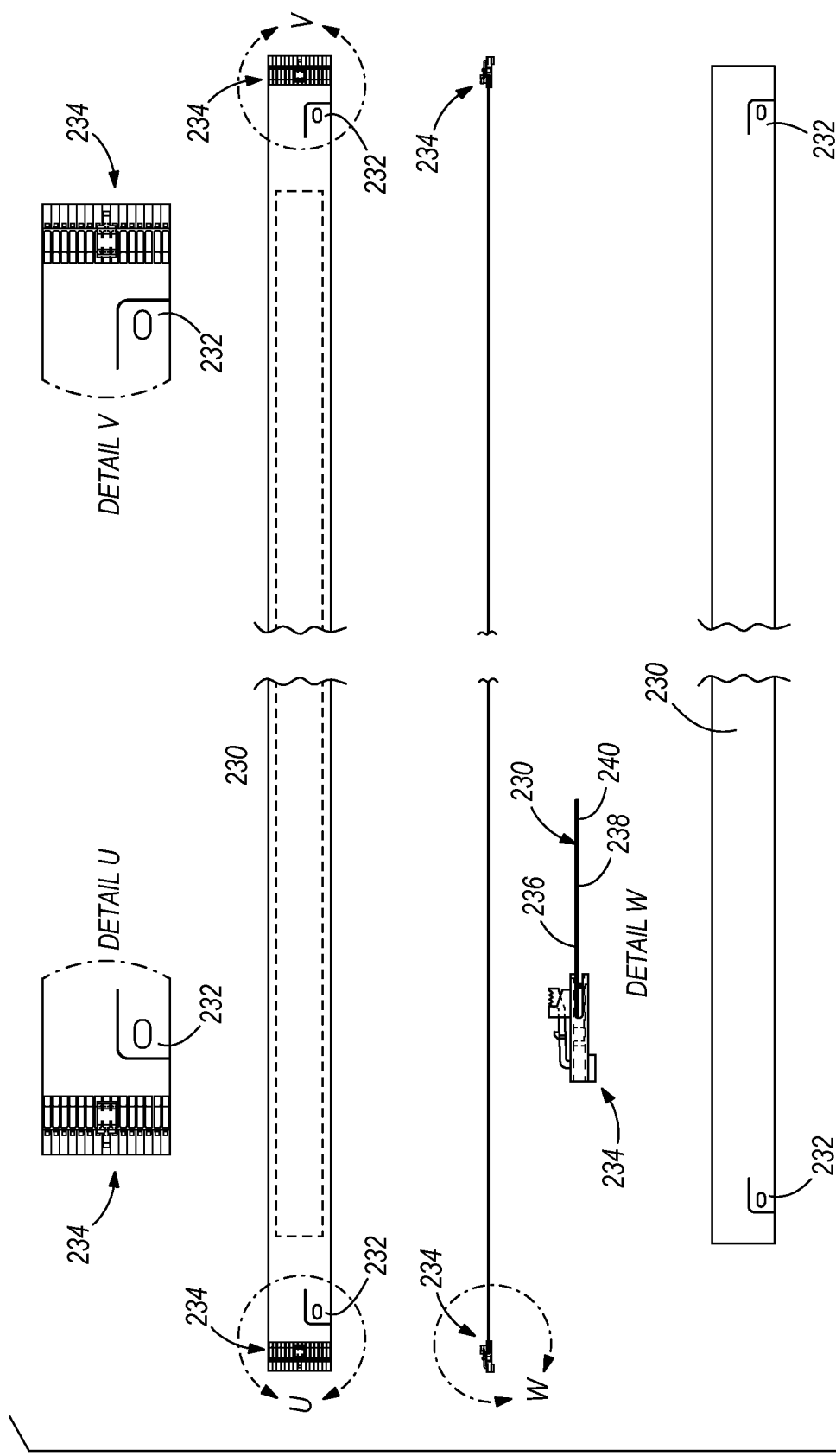
FIG. 18 includes a top, bottom, and side view of the flattened wiring of FIG. 17, illustrating connector ends.

In some embodiments, a pressure sensitive adhesive is applied to the bottom 225 of the channel 118 to hold the flattened wiring 230 in place. Using a pressure sensitive adhesive can eliminate the need for a plastic extrusion or similar additional mechanism to hold the wiring in place. The flattened wiring 230 can have a polyamide construction that is radiation resistant without the need for additional radiation hardened materials or protective coverings. As shown in FIG. 17, the flattened wiring 230 is plugged into receptacles integrated into the lower support 98 and/or another portion of the couch 82. As also shown in FIG. 17, the flattened wiring 230 also includes an integrated ground tab 232, which eliminates the need for a separate grounding mechanism. FIG. 18 illustrates the flattened wiring 230 according to one embodiment of the invention in more detail. As shown in FIG. 18, the flattened wiring 230 includes connector ends 234 that connect with the integrated receptacles on the lower support 98. The flattened wiring 230 also includes a plane layer 236 and a signal layer 238. The signal layer 238 is positioned on the bottom surface of the wiring 230, which also includes pressure sensitive adhesive 240.

The flattened wiring 230 can be used apart from or in combination with the above-described flattened channels 118. For example, in addition to the lower attenuation characteristics of the flattened wiring 230 resulting from its reduced thickness, the flattened wiring 230 also allows the channels 118 that receives and maintains the wiring 230 to be shallower. In particular, using the flattened wiring 230 allows the height of the sidewalls 224 of the channel 118 to be minimized while still maintaining the wiring 230 in its proper place. Thus, the angles Y and Z (see FIGS. 12 and 13) can be even more obtuse, producing a channel configuration with low attenuation.

It should be understood that the embodiments described above that solve various attenuation problems and issues can be combined or used separately. For example, the upper support 94 with the reinforced holes 200 can be used with a lower support 98 that includes flattened channels 18 and flattened wiring 230. Alternatively, each embodiment can be used independently of the other embodiments.

Various features and advantages of the invention are set forth in the following claims.

What is claimed is:

1. A patient support device for a radiation therapy treatment system, the device comprising:
a support having an upper surface facing a patient when the patient is positioned on the patient support device, the upper surface including at least one channel for wiring used to operate the patient support device, the channel including two sidewalls and a bottom wall and wherein at least one of the two sidewalls intersects the bottom wall at an obtuse angle in order to reduce or eliminate attenuation of a radiation beam.

2. The patient support device of claim 1, wherein the at least one channel has a depth approximately equal to a thickness of an electrical conductor positioned within the at least one channel.

3. The patient support device of claim 2, wherein the electrical conductor includes a flat flex cable.

4. The patient support device of claim 1, wherein the obtuse angle is from approximately 135 degrees to approximately 179 degrees.

5. The patient support device of claim 1, wherein at least one of the sidewalls directs a radiation beam aimed along the sidewall outside a patient treatment area of the patent support device.

6. The patient support device of claim 1, wherein the at least one channel extends down a length of the support.

7. The patient support device of claim 1, further comprising an upper support movable with respect to the first support and controlled by the wiring.

8. The patient support device of claim 7, further comprising a bearing layer between the upper surface of the first support and a lower surface of the upper support.

9. The patient support device of claim 1, wherein the wiring is adhered to the bottom wall.

10. The patient support device of claim 1, wherein the at least one channel includes a first channel and a second channel and wherein wiring included in the first channel includes wiring conveying power and wiring included in the second channel includes wiring conveying data.

11. A patient support device for a radiation therapy treatment system, the device comprising:

a support having an upper surface facing a patient when the patient is positioned on the patient support device, the upper surface including at least one channel and flat flex cable used to operate the patient support device positioned within the at least one channel, wherein the at least one channel includes two sidewalls and a bottom wall and wherein at least one of the two sidewalls intersects the bottom wall at an obtuse angle in order to reduce or eliminate attenuation of a radiation beam.

12. The patient support device of claim 11, wherein the at least one channel has a depth approximately equal to a thickness of the flat flex cable.

13. The patient support device of claim 11, wherein the obtuse angle is from approximately 135 degrees to approximately 179 degrees.

14. The patient support device of claim 11, wherein at least one of the two sidewalls directs a radiation beam aimed along the sidewall outside a patient treatment area of the support.

15. The patient support device of claim 11, wherein the at least one channel extends down a length of the support.

16. The patient support device of claim 11, further comprising an upper support movable with respect to the first support and controlled by the flat flex cable.

17. The patient support device of claim 16, further comprising a bearing layer between the upper surface of the first support and a lower surface of the upper support.

18. The patient support device of claim 11, wherein the flat flex cable is adhered to the at least one channel.

19. The patient support device of claim 11, wherein the at least one channel includes a first channel and a second channel and wherein wiring included in the first channel includes wiring conveying power and wiring included in the second channel includes wiring conveying data.

* * * * *